United States Patent
Nakano

(10) Patent No.: US 9,320,423 B2
(45) Date of Patent: Apr. 26, 2016

(54) IMAGE PROCESSING APPARATUS FOR DETECTING BOUNDARIES IN TOMOGRAPHIC IMAGE, METHOD FOR IMAGE PROCESSING, IMAGE PICKUP SYSTEM, AND COMPUTER-READABLE STORAGE MEDIUM

(75) Inventor: Yuta Nakano, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 590 days.

(21) Appl. No.: 12/966,950

(22) Filed: Dec. 13, 2010

(65) Prior Publication Data

US 2011/0141259 A1    Jun. 16, 2011

(30) Foreign Application Priority Data

Dec. 15, 2009   (WO) ................ PCT/JP2009/070924

(51) Int. Cl.
| | |
|---|---|
| A61B 3/10 | (2006.01) |
| A61B 3/00 | (2006.01) |
| A61B 5/00 | (2006.01) |
| G06T 7/00 | (2006.01) |

(52) U.S. Cl.
CPC .............. *A61B 3/0025* (2013.01); *A61B 3/102* (2013.01); *A61B 5/0066* (2013.01); *A61B 5/4893* (2013.01); *G06T 7/0083* (2013.01); *G06K 2209/05* (2013.01); *G06T 7/0012* (2013.01); *G06T 2207/10024* (2013.01); *G06T 2207/10072* (2013.01); *G06T 2207/10101* (2013.01); *G06T 2207/30041* (2013.01)

(58) Field of Classification Search
CPC .... A61B 3/0025; A61B 3/102; A61B 5/0066; A61B 5/4893; G06T 2207/30041; G06T 7/0012; G06T 2207/10024; G06T 2207/10072; G06T 7/0083; G06T 2207/10101; G06K 2209/05

See application file for complete search history.

(56) References Cited

U.S. PATENT DOCUMENTS

| 7,347,548 B2 | 3/2008 | Huang |
| 2010/0194757 A1 | 8/2010 | Tomidokoro |
| 2011/0299034 A1* | 12/2011 | Walsh et al. ................. 351/206 |

FOREIGN PATENT DOCUMENTS

| JP | 2009-160190 A | 1/2000 |
| JP | 2009-183332 A | 1/2000 |
| JP | 2009-066015 A | 4/2009 |
| WO | WO2009/034704 A1 | 3/2009 |

OTHER PUBLICATIONS

Tomidokoro et al. (English Translation of JP Pub. No. 2009-066015 A).*

* cited by examiner

*Primary Examiner* — Joseph Ustaris
*Assistant Examiner* — Jill Sechser
(74) *Attorney, Agent, or Firm* — Canon U.S.A., Inc., IP Division

(57) ABSTRACT

An image processing apparatus includes a detecting means for detecting a plurality of boundaries of layers in a tomographic image of a subject's eye, and identifying means for identifying the kinds of the detected boundaries on the basis of the characteristics of the layer between the detected boundaries and those of the vitreous body of the subject's eye.

13 Claims, 10 Drawing Sheets

IMAGE PROCESSING APPARATUS FOR DETECTING BOUNDARIES IN TOMOGRAPHIC IMAGE, METHOD FOR IMAGE PROCESSING, IMAGE PICKUP SYSTEM, AND COMPUTER-READABLE STORAGE MEDIUM

TECHNICAL FIELD

The present invention relates to an image processing apparatus, a method for image processing, an image pickup system, and a computer-readable storage medium which are for identification of layers in a tomographic image of an eye.

BACKGROUND ART

Eye examinations have been widely performed for the purpose of early diagnosis of diseases which top the list of lifestyle-related diseases and causes of blindness. Tomographic eye image pickup device, such as optical coherence tomography (OCT), are useful for disease diagnosis because a state in retinal layers can be three-dimensionally observed through the device.

The retina at the back of an eye has a layered structure including a plurality of layers. Information concerning the layered structure, e.g., the thickness of each layer, is used as an objective indicator to measure the extent of a disease. In order to use such an indicator, a technique of analyzing a tomographic image of the retina to accurately determine the layered structure and identifying the kind of boundary between layers is important.

U.S. Pat. No. 7,347,548 discloses a technique of detecting two strong edges in the depth direction in a tomographic image and identifying the edge adjacent to the shallow side as a boundary corresponding to the inner limiting membrane and the edge adjacent to the deep side as a boundary corresponding to the retinal pigment epithelium. This technique focuses on that the inner limiting membrane and the retinal pigment epithelium, serving as retinal tissue, appear as strong edges in a tomographic image.

WO publication 2009034704 A1 discloses, as a technique of determining a change in layered structure, a technique of determining the presence or absence of an artifact of a blood vessel. This technique utilizes that a signal remarkably attenuates in a region under a blood vessel to provide uniform image characteristics and is intended to determine the presence or absence of an artifact on the basis of pixel values in the vicinity of the boundary of a layer.

For example, in case of vitreous cortex detachment, the vitreous cortex floats above the inner limiting membrane. According to the technique disclosed in U.S. Pat. No. 7,347,548, the vitreous cortex may be erroneously detected as the inner limiting membrane. As described above, it is difficult to accurately identify the boundaries of retinal layers according to change in the layered structure due to a disease or change in imaging region or conditions.

Furthermore, for response to not only artifacts but also a change in the layered structure, the characteristics of the retinal layers remarkably vary depending on position in the depth direction. Accordingly, the boundary of a layer cannot be accurately identified on the basis of only a state in the vicinity of the boundary of the layer as disclosed in WO publication 2009034704 A1.

SUMMARY OF INVENTION

The present invention has been made in order to solve the problem and provides including detecting means for detecting a plurality of boundaries of layers in a tomographic image of a subject's eye, and identifying means for identifying the kind of each of the detected boundaries on the basis of characteristics of the layer between the detected boundaries and those of the vitreous body of the subject's eye.

Further features of the present invention will become apparent from the following description of exemplary embodiments with reference to the attached drawings.

DESCRIPTION OF EMBODIMENTS

First Embodiment

A tomographic image pickup system according to a first embodiment will be described in accordance with FIG. 1. In the tomographic image pickup system, a tomographic image acquisition device 20 acquires a tomographic image of a subject's eye and an image processing apparatus 10 generates information about edge components and a median image from the tomographic image. Layers in the retina corresponding to the edge components are identified on the basis of characteristics between feature points extracted from the median image and those of the vitreous body.

The image processing apparatus 10 is communicably connected to the tomographic image acquisition device 20 and a storage unit 30. The tomographic image acquisition device 20 captures an image of the subject's eye in accordance with an operation by an operator (not illustrated) and transmits the captured image to the image processing apparatus 10 and the storage unit 30.

The tomographic image acquisition device 20 is, for example, an OCT image pickup device using optical coherence tomography (OCT). This OCT image pickup device generates coherent light from reflected light and scattered light (returning light) in a subject irradiated with signal light and reflected light of reference light applied to a reference object, and analyzes the coherent light, thus forming an image of the internal structure of the subject. When the subject has a layered structure, the image of the layered structure can be formed on the basis of the intensities of returning light, serving as reflected or scattered light in layers. In the OCT image pickup device, a predetermined point on the retina is irradiated with signal light to obtain information about the depth direction at the point (A-scan). The A-scan is performed at regular intervals on a predetermined line on the surface of the retina (B-scan) and information items obtained by the B-scans are combined, thus obtaining a tomographic image of the retina. When the A-scan is performed in a predetermined range on the surface of the retina, a plurality of tomographic images can be obtained. In addition, when those images are reconstructed, three-dimensional volume data can be obtained. Thus, an image (C-scan image) of the retina at arbitrary depth can also be obtained.

Figure 1:
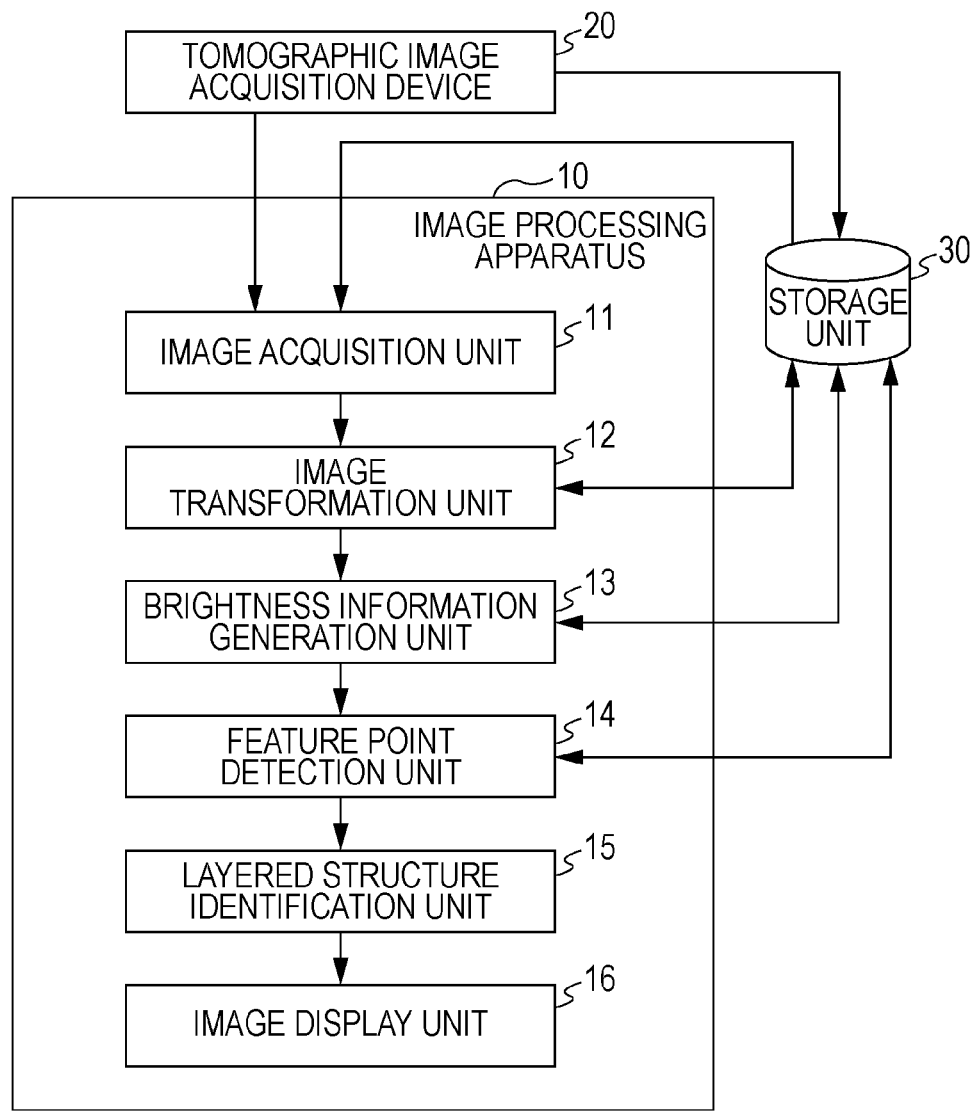
FIG. 1 is a diagram of the configuration of a tomographic image pickup system according to a first embodiment.

The image processing apparatus 10 includes, for example, blocks illustrated in FIG. 1 as circuits. In another example, the image processing apparatus 10 includes a known electronic computer. Functions corresponding to the blocks are realized by the cooperation between hardware and software. Specifically, the electronic computer includes, for example, a CPU, a ROM, a RAM, an HDD, a mouse, a keyboard, a network I/F, and a display unit. In this case, the ROM or HDD stores a program for realizing a process illustrated in FIG. 3 which will be described later. This program is developed in the RAM and the CPU executes instructions of the program, thus exhibiting the functions illustrated in FIG. 1 and realizing the process illustrated in FIG. 3.

The functions of the image processing apparatus 10 will be described. An image acquisition unit 11 acquires a tomographic image from the tomographic image acquisition device 20. The image acquired by the image acquisition unit 11 is subjected to predetermined processes by an image transformation unit 12, a brightness information generation unit 13, a feature point detection unit 14, and a layered structure identification unit 15, thus determining the layered structure. After that, the layered structure is displayed on an image display unit 16 including a liquid crystal display or the like.

As described above, a tomographic image by OCT is obtained using returning light reflected or scattered from the layers of the retina. Accordingly, a feature appears in the boundary of a layer in which reflection or scattering tends to occur. Therefore, the analysis of an OCT image uses an approach to specifying the boundary of a layer to determine the layered structure.

The image transformation unit 12 obtains transformed images, necessary for identification of the layered structure, from the acquired tomographic image. In the present embodiment, edge-enhanced images used mainly for specifying the boundaries of layers and a smoothed image used for specifying a layer between the boundaries are generated. As for the edge-enhanced images, a Sobel image in which edges from low to high pixel value as viewed from the shallow side of the layers are enhanced and a Sobel image in which edges from high to low pixel value as viewed from the shallow side are enhanced are generated. These Sobel images can be generated by applying a known Sobel filter to each A-scan line of the tomographic image, serving as an original image, with predetermined parameters. As for the smoothed image, a median image obtained through a known median filter is used. Pixel values between edges in the median image are referred to.

The method for image transformation is not limited to the above. For example, a smoothing filter, e.g., an averaging filter can be used instead of the median filter. In addition to the smoothing filter and the edge enhancing filter in the present embodiment, image transformation may be performed using, for example, a grayscale transformation filter for gamma correction or a morphological filter.

The brightness information generation unit 13 creates brightness profiles, serving as brightness information, from the Sobel images generated by the image transformation unit 12. In this instance, the term "brightness profile" is a sequence of brightness values of pixels in the depth direction on one A-scan line and is a graph of brightness values in the depth direction. In the present embodiment, since the A-scan line is scanned at intervals of a 5-pixel width on a tomographic image of 256 (width) by 250 (height) pixels, 50 brightness profiles are created from one tomographic image. This processing is performed on the Sobel images and the median image input from the preceding step and the created profiles are stored into the storage unit 30.

The feature point detection unit 14 extracts feature points from the created brightness profiles. Since reflected signal light increases in the boundary of a layer, edges in the image are extracted, so that the locations of the boundaries of the layers can be specified. In this case, maximum points (hereinafter, referred to as "peaks") in each brightness profile created from the Sobel image are examined and are detected as a plurality of feature points. As a result of detection, information indicating the position and magnitude of each peak for each A-scan line is stored into the storage unit 30.

The layered structure identification unit 15 identifies the kind of the boundary of each layer in the retina or the kind of layer. The term "identification" means to determine which layer in the retina corresponds to the feature point detected by the feature point detection unit 14, namely, the kind of layer.

The layered structure identification unit 15 obtains brightness values between the peaks, obtained from the brightness profiles created from the Sobel images, from the median image and compares the brightness values with a brightness value of the vitreous body to determine the layered structure between the peaks, thus identifying the kinds of the boundaries of the layers corresponding to the peaks on the basis of the comparison result. Even if the boundaries of the layers are specified, the retina does not have a simple layered structure and further includes the macula lutea and the optic disk. For example, glaucoma or partial detachment of the vitreous cortex may occur on the retina. If the layered structure is simple, signal light is absorbed by a blood vessel, so that tissue below the blood vessel cannot be subjected to imaging. Accordingly, the layered structure may look changed. Identification error due to the above circumstances can be reduced using information about the layered structure between the peaks. This process will be described in detail later.

An image showing the above specified layered which are color-coded according to kind is generated and is displayed on the image display unit 16. Consequently, a diagnostician can visually confirm the layered structure of the retina. In addition, the thickness of a specified layer is automatically extracted from the image and a thickness graph is formed, so that diagnostic indicators can be converted into numbers and be confirmed.

Figure 2A:
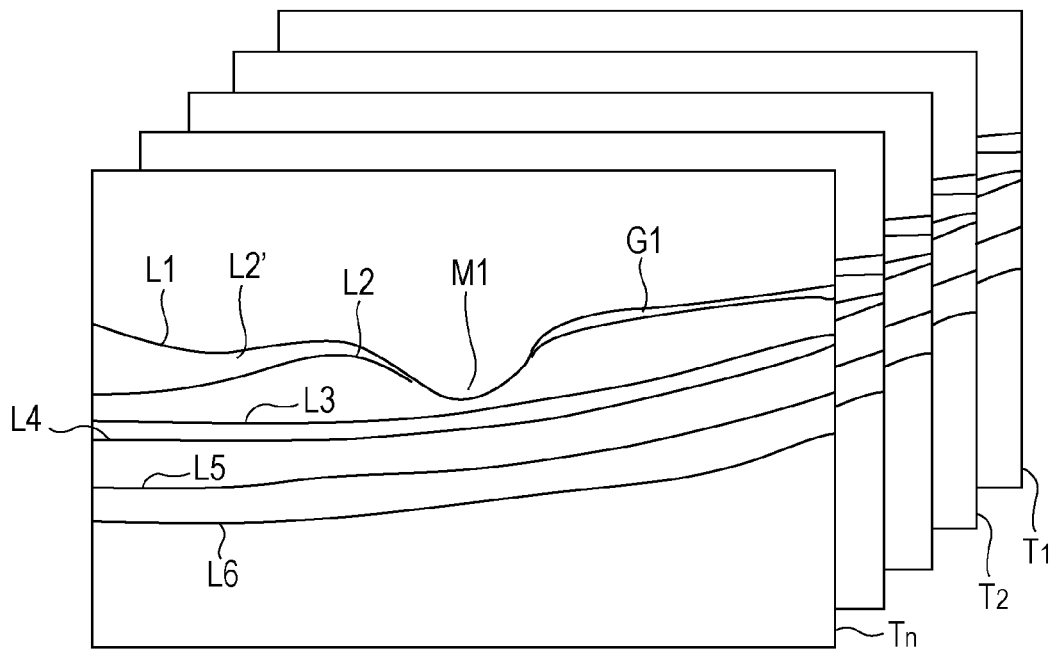
FIGS. 2A and 2B are diagrams each illustrating an exemplary layered structure of a retina serving as an imaging subject.

The structures of the retinal layers to be subjected to the process of identifying the layered structure in accordance with the present embodiment will be described below with reference to FIGS. 2A and 2B. FIG. 2A illustrates a schematic diagram of tomographic images of the macula lutea of the retina. The locations of the boundaries of layers are indicated by solid lines. Each of two-dimensional tomographic images (B-scan images, which will be referred to as "tomographic images" hereinafter) T1 to Tn of the macula lutea is a two-dimensional image obtained by performing A-scan on one line on the surface of the retina. Since A-scan is performed not continuously but at regular intervals on one line, the gap between the adjacent A-scans is interpolated by a predetermined interpolation method, thus forming the two-dimensional image.

In the tomographic image Tn, an inner limiting membrane (ILM) L1, the boundary (hereinafter, referred to as "nerve fiber layer boundary") L2 between a nerve fiber layer (NFL) and a layer underlying it, and the nerve fiber layer L2' are illustrated. In addition, the boundary (hereinafter, referred to as "inner plexiform layer boundary") L3 between an inner plexiform layer and a layer underlying it, the boundary (hereinafter, referred to as "outer plexiform layer boundary") L4 between an outer plexiform layer and a layer underlying it, the boundary L5 of the interface between inner and outer segments of the photoreceptors (IS/OS), and the lower boundary L6 of a retinal pigment epithelium are illustrated. In some cases, the boundary of the IS/OS and that of the RPE cannot be distinguished from each other depending on the performance of an OCT image pickup device. In the present invention, this accuracy is not significant. In addition, although the inner limiting membrane (ILM) and the interface between inner and outer segments of the photoreceptors (IS/OS) can be seen as layers, they are regarded as boundaries because they are very thin.

The retina typically has such a simple layered structure. However, the retina may have a structure different from this depending on region or lesion. There is no nerve fiber layer in the macular depression M1. A region G1 exhibits a state of glaucoma. The nerve fiber layer is thin. A patient with glaucoma has such a symptom. Accordingly, the thickness of the nerve fiber layer serves as a quantitative indicator indicating the degree of progression of a disease, such as glaucoma, or the extent of recovery after treatment.

Figure 2B:
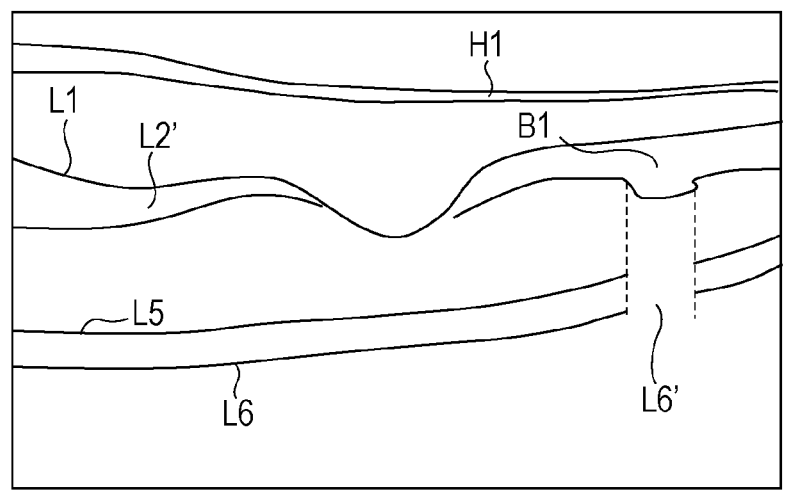

FIG. 2B similarly illustrates a tomographic image of the macula lutea of the retina. In this case, a state of detachment of a vitreous cortex H1 above the inner limiting membrane L1 due to a disease or the like is illustrated. There is a gap between the inner limiting membrane L1 and the vitreous cortex H1 and there is no retinal tissue.

If there is a blood vessel B1, signal light attenuates due to red blood cells in the blood vessel. Accordingly, a region under the blood vessel is not imaged. Disadvantageously, an artifact L6' occurs.

Abnormality, such as a lesion, or a large change in structure appears in the layers in a range from the inner limiting membrane L1 to the boundary L6 of the retinal pigment epithelium. Accordingly, these layers are specified and the layers included in these layers are specified.

Figure 3:
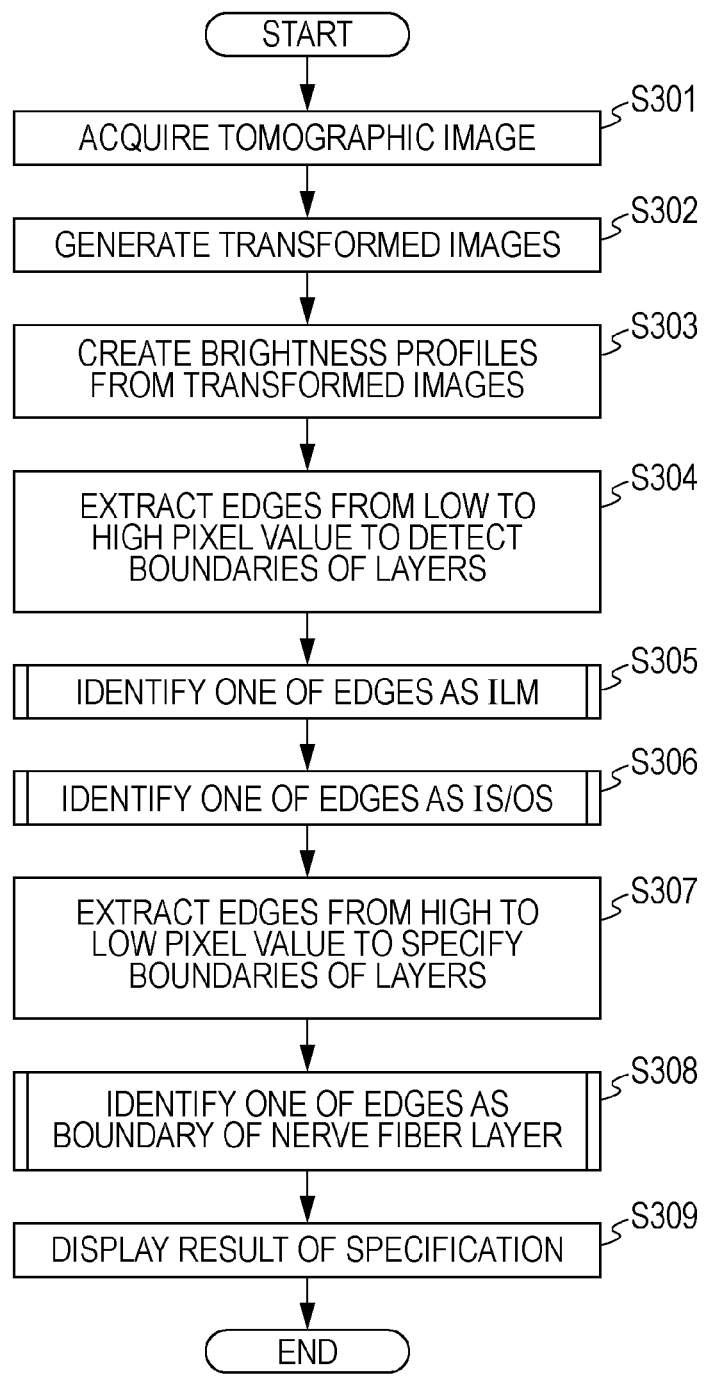
FIG. 3 is a flowchart illustrating the flow of a process by an image processing apparatus.

The flow of the process of identifying the layered structure by the functions of the above-described image processing apparatus 10 will be described below in accordance with a flowchart of FIG. 3. In order to identify layer boundaries, this process is a process of determining the tissue between the layer boundaries to identify the layer boundaries on the basis of the result of determination.

In step S301, the image acquisition unit 11 acquires an OCT tomographic image captured by the tomographic image acquisition device 20. When a region to be captured is designated and is captured by the tomographic image acquisition device 20, information about the region, e.g., the macula lutea or the optic disk is also acquired. Using this region information, a proper parameter for image processing can be determined.

In step S302, the image transformation unit 12 performs image transformation on each OCT tomographic image acquired by the image acquisition unit 11. In the present embodiment, the median filter and the Sobel filter are applied to the tomographic image, thus generating images (hereinafter, referred to as "median image" and "Sobel images"). In this case, it is assumed that when the signal intensity is high, the pixel value is high and, when the signal intensity is low, the pixel value is low. The image transformation unit 12 transmits the transformed images to the brightness information generation unit 13 and stores the images into the storage unit 30.

In step S303, the brightness information generation unit 13 creates brightness profiles, serving as brightness information, from the images transformed in step S302. It is not always necessary to graph brightness values. Pixel values of the images or signal intensities may be imaged. When the brightness profiles are created using the Sobel images, noise is removed from the images. Accordingly, edges can be easily detected. In addition, creation of the profiles using the median image has effects that the occurrence of noise which particularly becomes a problem in an OCT image can be suppressed and the tendency of an image in a predetermined range can be easily grasped.

It is not always necessary to create the brightness profiles from the transformed images. Edges having a predetermined intensity can be extracted from a tomographic image, serving as an original image.

In step S304, the feature point detection unit 14 detects peaks from the brightness information generated in step S303, thus specifying the locations of layer boundaries. Since the Sobel images are edge-enhanced images, detecting a peak from the brightness information is synonymous with detecting a point at which a change from low to high intensity of signal light is large, namely, an edge from low to high pixel or brightness value in a tomographic image. A threshold value determined experimentally or based on image information is used for detection.

As described above, a sign of a lesion appears in the area between the inner limiting membrane and the boundary of the IS/OS. It is therefore important to specify these layers. In the structures of the retinal layers, the inner limiting membrane is the boundary between the background (vitreous body) having low pixel values and the retinal tissue having relatively high pixel values and can be detected as the above-described edge. Since the IS/OS is in contact with relatively dark tissue as viewed from the shallow side of the layers, it can be detected as the above-described edge. In the retina, the inner limiting membrane and the IS/OS can be easily detected as strong edges because they strongly reflect or scatter the signal light. Except for the boundary of the vitreous cortex, other boundaries corresponding to edges from low to high intensity as viewed from the shallow side of the layers are not large edges. Accordingly, a threshold value is adjusted so that the inner limiting membrane and the IS/OS can be preferentially extracted in that manner.

Furthermore, the tissue between the inner limiting membrane and the IS/OS includes layers corresponding to further enhanced edges from high to low intensity. Accordingly, the edges are detected to specify the layers between the inner limiting membrane and the IS/OS.

This detection is performed for each A-scan line. The reliability of detection can be increased using not signals obtained by interpolation but actually measured values.

The peaks detected as described above indicate the locations of the boundaries of the layers.

In step S305, the layered structure identification unit 15 identifies one of the boundaries of the retinal layers, obtained using the peaks detected in step S304, as the inner limiting membrane (ILM). From the viewpoint of the structure of retinal tissue, the interface between the vitreous body, which is typically excluded in the retinal tissue and serves as a background region, and the retinal tissue is the inner limiting membrane. However if there is detachment of the vitreous cortex, the structure differs. Accordingly, whether the area between the two peaks detected as viewed from the shallow side is the background or the retinal tissue is determined using the profiles obtained from the median image. If it is the background, the first peak from the shallow side is the vitreous cortex and the next peak is the inner limiting membrane (ILM). If the area between the peaks is the retinal tissue, the first peak is identified as the inner limiting membrane. The processing will be described in detail later.

In step S306, the layered structure identification unit 15 identifies one of the boundaries of the retinal layers obtained using the peaks detected in step S304 as the IS/OS. In this case, the tissue between the inner limiting membrane and the boundary of the layer located deeper than the inner limiting membrane is determined and the IS/OS is identified on the basis of the result of determination. The processing will be described in detail later.

In step S307 and subsequent steps, the boundaries of the layers located between the identified inner limiting membrane and IS/OS are identified (first identification). The feature point detection unit 14 detects peaks in the brightness profiles using a predetermined threshold value, thus detecting points at each of which the signal light remarkably changes from high to low intensity as viewed from the shallow side of the layers. Since the inner limiting membrane and the IS/OS have already been identified and the area between these boundaries to be subjected to analysis is specified, a threshold value for peak detection and setting of parameters can be appropriately set in the following nerve fiber layer identification (second identification).

In step S308, the layered structure identification unit 15 identifies one of the boundaries of the retinal layers obtained using the peaks detected in step S307 as the boundary of the nerve fiber layer. In this instance, the layered structure between the inner limiting membrane and each peak obtained in step S307 are determined to identify the nerve fiber layer boundary. The reason is as follows. Depending on glaucoma or depression, the nerve fiber layer boundary may disappear or be thin to such an extent that the layer cannot be specified as an image. In this case, the nerve fiber layer boundary substantially matches the inner limiting membrane. Disadvantageously, identification error may occur. This processing will also be described later.

In step S309, the specified boundaries of the layers are color-coded according to identified kind and the boundaries are superimposed on the tomographic image. The image display unit 16 displays the resultant image. A table showing the relationship between the layer boundaries and the colors is previously stored in the storage unit 30. A display screen is generated on the basis of this data.

As described above, the kind of tissue between specified boundaries in an image is determined and the kind of each layer boundary is identified on the basis of the result of determination. Advantageously, identification error can be reduced.

In addition, the ILM and the IS/OS are specified on the basis of points each representing the transition from low to high signal intensity as viewed from the shallow side and the layered structure between the boundaries is then identified on the basis of points each representing the opposite transition, so that the boundaries important for diagnosis can be easily specified. In addition, the layered structure in the area between the boundaries where a sign of a lesion tends to occur can be specified accurately.

In addition, since the pixel value or brightness value of the vitreous body is used, the kind of layer can be properly determined because such a value is a threshold value more suitable for specifying capturing conditions or an image than determination using a fixed threshold value.

Figure 4:
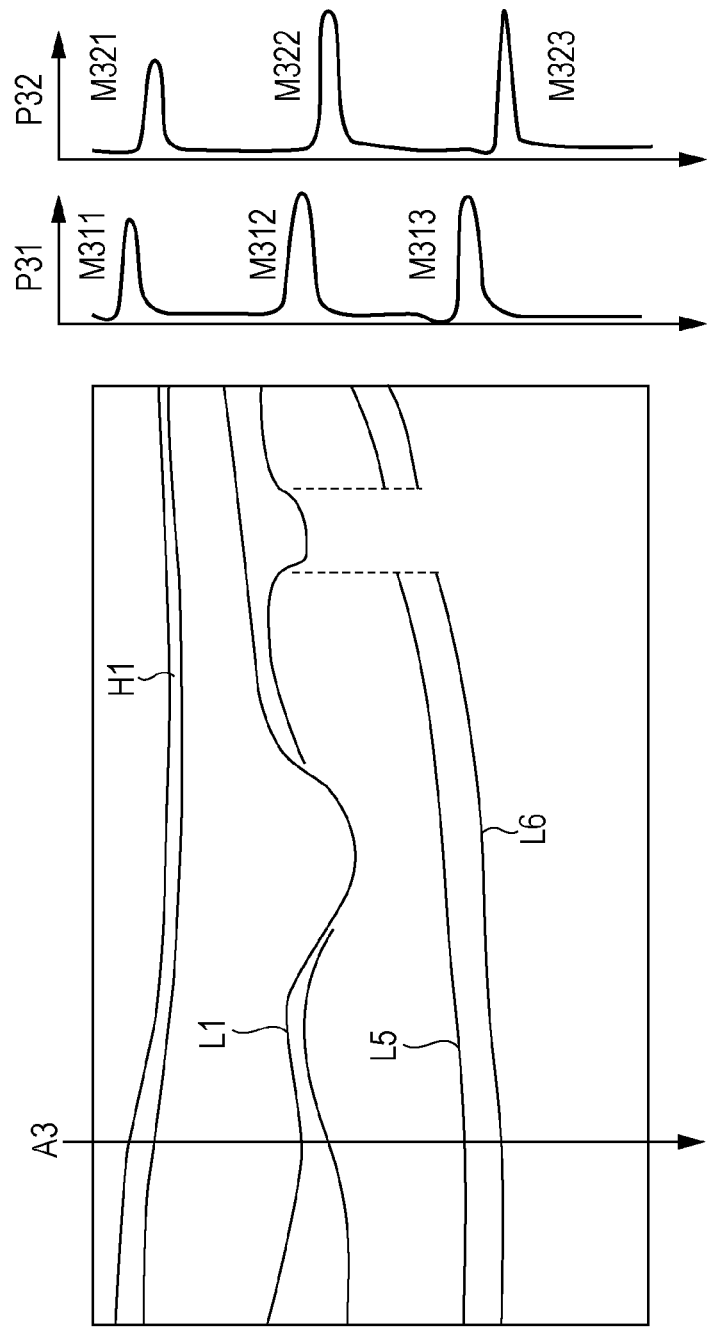
FIG. 4 illustrates exemplary brightness profiles related to an A-scan line in the retina.

FIG. 4 is a diagram illustrating the relationship between a tomographic image of a retina, an A-scan line, and brightness profiles. For a one-dimensional image obtained by performing A-scan at the position of a line A3, there is illustrated a profile P31 in one Sobel image in which edges from low to high pixel value are enhanced. In addition, there is illustrated a profile P32 in the other Sobel image in which edges from high to low pixel value are enhanced. A peak M311 indicates the boundary between the background and the vitreous cortex, a peak M312 indicates the boundary between the gap and the inner limiting membrane, and a peak M313 indicates the location of the IS/OS. A peak M321 indicates the boundary between the vitreous cortex and the gap, a peak M322 indicates the boundary of the nerve fiber layer, and a peak M323 indicates the boundary of the retinal pigment epithelium. In step S304, the feature point detection unit 14 detects the peaks for each A-scan line and stores the position and magnitude of each peak into the storage unit 30.

Process for Inner Limiting Membrane

Figure 5:
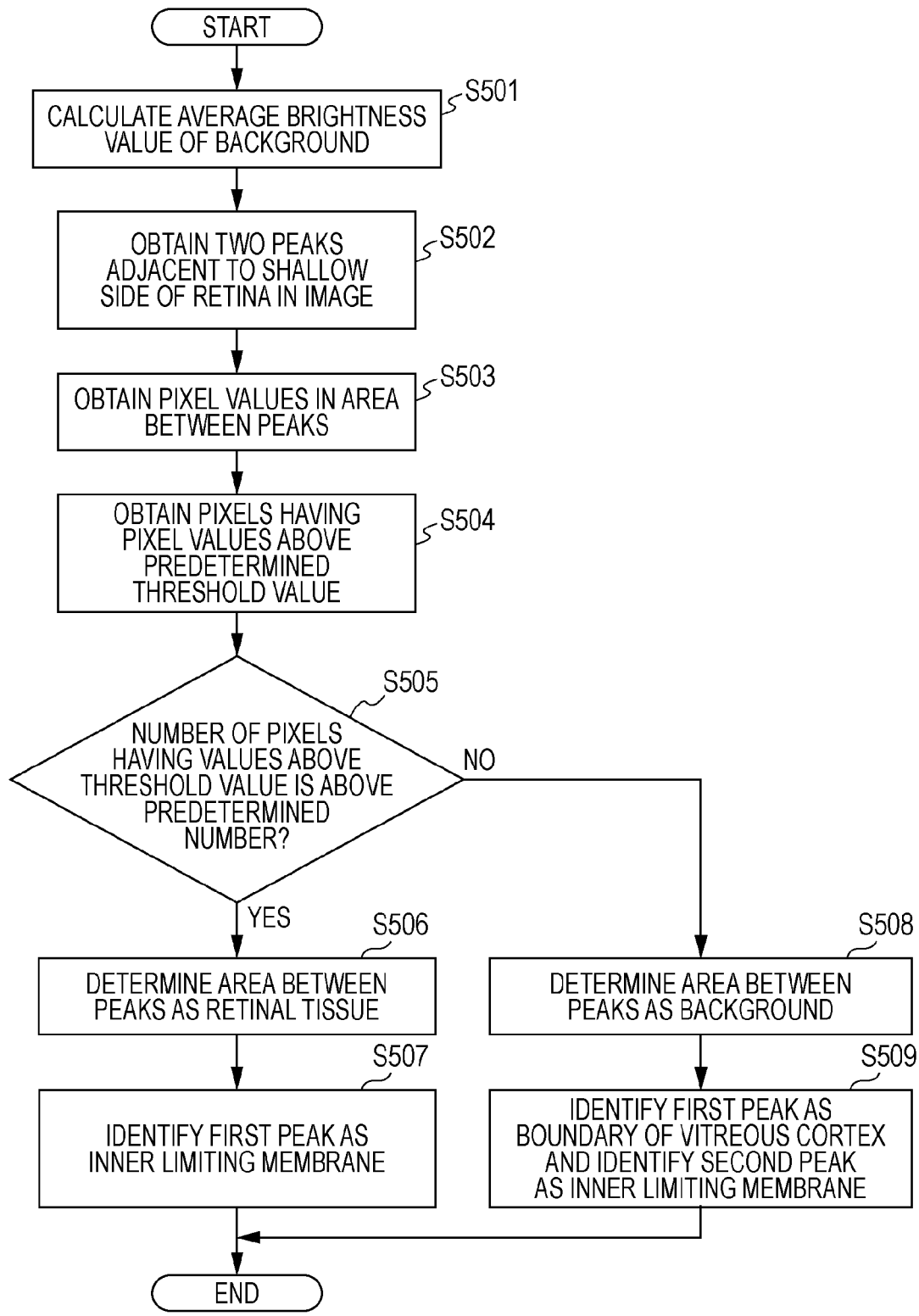
FIG. 5 is a flowchart illustrating the flow of an ILM identifying process by the image processing apparatus.

The details of the processing for identifying the inner limiting membrane L1 (ILM) in step S305 will be described in accordance with FIG. 5. In step S501, the layered structure identification unit 15 first calculates an average brightness value of an approximate background (region other than the retinal layers in the image). In the present embodiment, a target is set to only a region having values at or below an experimentally determined threshold value in the median image and an average brightness value thereof is calculated. Such threshold processing is performed, thus removing noise components included in part having high brightness values. The method of calculating an average brightness value of the background is not limited to this. A threshold value may be determined by, for example, determination analysis or the P-tile method. An average brightness value may be calculated using brightness values at the upper or lower end, where the retinal layer does not exist, of an image.

Subsequently, in step S502, the layered structure identification unit 15 examines the positions of the peaks detected in step S304 and sequentially sets two peaks to first and second peaks in the order from the shallow side of the layers. In this case, although detection is performed using the profile P31 in FIG. 4, detection may be performed using the profile P32. This processing is performed on each A-scan line. After the first and second peaks are determined, the layered structure identification unit 15 examines a brightness profile between the two peaks in the median image. In step S504, the layered structure identification unit 15 performs processing for determining whether the area between the peaks corresponds to the background (vitreous region) or the retinal tissue. Specifically, pixels each having a pixel value above the product of the average pixel value of the background and a coefficient of 1.2 are obtained from pixels existing between the first and second peaks. In step S505, the layered structure identification unit 15 determines the proportion of the pixels included between the boundaries. Although the coefficient is an experimentally obtained value, the coefficient is not limited to this. A threshold value may be dynamically determined according to image information, such as an average value in a brightness profile.

If the calculated proportion is above ½ (Yes in step S505), it is determined that the retinal tissue exists between the peaks (step S506). The first peak is identified as the inner limiting membrane L1 (step S507). If the calculated proportion is at or below ½ (No in step S505), it is determined that the area between the peaks is the background (step S508). The second peak is identified as the inner limiting membrane L1. Simultaneously, the first peak is determined as the vitreous cortex H1 (step S509).

Conditions for determining the inner limiting membrane are not limited to the above. For example, the coefficient by which the average value of the background is multiplied may be dynamically obtained from a histogram of the image. Furthermore, in the present embodiment, whether the area between the peaks corresponds to the retinal tissue or the background is determined on the basis of brightness information, namely, the proportion of the pixels having pixel values above the threshold value. The determination is not limited to this. For example, a gradient may be obtained from the brightness profile and be used as an indicator for determination. Alternatively, feature values may be obtained from brightness information and be input to a discrimination circuit for determination. Conditions for determination using the distance between the peaks are not limited to this. The conditions may be dynamically obtained according to scale of an image.

As described above, tissue between the peaks is determined and the kind of layer boundary is identified on the basis of the result of determination, so that identification error can be prevented.

Process for IS/OS

The details of processing for identifying the IS/OS L5 in step S306 will be described in accordance with FIG. 6. In this process, in addition to the processing for determining tissue between the peaks, two-phase processing is performed in order to address an artifact caused by a blood vessel or bleeding.

In step S601, the layered structure identification unit 15 obtains a peak positioned deeper than the location of the inner limiting membrane specified by the above-described processing. In this stage, a plurality of peaks may be obtained.

In step S602, the layered structure identification unit 15 determines whether the peak obtained from each A-scan line satisfies predetermined conditions. Only the peak satisfying the conditions for specifying is specified as the IS/OS L5. In the present embodiment, two items, the magnitude of the peak and the distance between the peaks are used as the specifying conditions for the IS/OS L5. As for the specifying condition based on the magnitude of the peak, the product of the magnitude of the peak of the inner limiting membrane L1 specified on the same A-scan line and 0.8 is set to a threshold value. As for the specifying condition based on the distance between the peaks, the peak has to be located at a predetermined distance or more from the inner limiting membrane L1 specified on the same A-scan line and be located below it in the image space. For these conditions, experimentally obtained values are used. If the peak satisfies these two conditions (Yes in step S602), the peak is specified as a candidate layer boundary for the IS/OS L5. This is the first-phase specifying processing.

Processing in steps S603 to S607 is the same as that for the above-described inner limiting membrane. In step S603, the layered structure identification unit 15 obtains pixel values between the peaks from the median image.

In step S604, the layered structure identification unit 15 obtains pixels having the pixel values above the predetermined threshold value from among the obtained pixel values between the peaks. In this case, a determination is made as to whether the layered structure between the peaks corresponds to the background (vitreous body) or the retinal tissue. This processing is for confirmation when the inner limiting membrane is erroneously identified due to noise or the like. For a threshold value, for example, pixels each having a pixel value higher than 1.2 times the average pixel value of the background are obtained. This threshold value is experimentally determined. This determination processing is not limited to the determination of whether the layered structure between the peaks is the background. Whether the layered structure between the peaks includes the nerve fiber layer or whether it includes an artifact caused by a blood vessel may be determined.

In step S605, the layered structure identification unit 15 determines whether the number of pixels having pixel values above the threshold value is above a predetermined number or proportion. For example, ½ is used. If it is determined that the number of pixels is above the predetermined number (Yes in step S605), the area between the peaks is determined as part in the retinal tissue (step S606). The obtained peak is identified as the IS/OS L5 (step S607).

On the other hand, when the peak does not meet the conditions of the candidate for the IS/OS L5 in step S602 (No in step S602), it is determined that any candidate for the IS/OS is not found on the A-scan line. The area is determined as an unidentifiable area and is stored into the storage unit 30 in the image processing apparatus 10 (step S608).

In step S609, processing for specifying the IS/OS in the area determined as the unidentifiable area in step S608 is performed. This is the second-phase specifying processing. This processing is performed to identify the IS/OS using the location and brightness value of the identified boundary and brightness values of the unidentifiable area in consideration of the continuity. The concrete processing will be described with reference to FIG. 7B.

If it is determined as No in step S605, the identifying process outputs an error (step S610) and the process terminates. Such a case is caused, for example, when setting of an imaging range has a problem, alternatively, when the retinal layers have abnormal structure. In this case, abnormality important for diagnosis may be included. Accordingly, the error may be informed of the user with speech or text information.

As described above, after the tissue between the peaks is determined, the detected layer boundary is identified as the IS/OS L5. This can prevent such an error that even if the retinal layers have abnormality, processing is performed while the retinal layers are being regarded as normal.

In addition, first specifying is performed on the basis of information for each A-scan line and second specifying made in consideration of the continuity of the interface based on the specified layer boundary is performed using brightness values of an area which cannot be specified. Accordingly, the layered structure can be accurately specified.

Figure 7A:
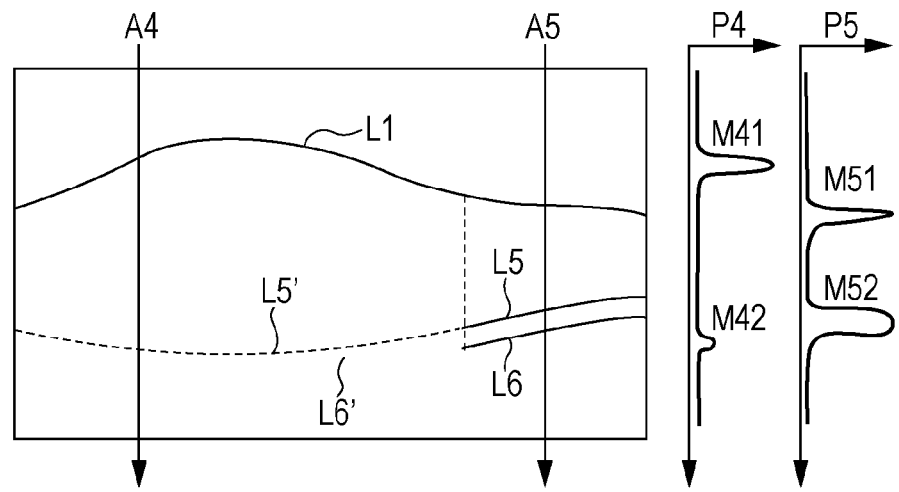
FIGS. 7A and 7B are diagrams illustrating the details of the RPE identifying process.

FIG. 7A is a diagram illustrating the relationship between A-scans in an area with a blood vessel or bleeding and profiles. A profile P5 is obtained by A-scan at a position A5. Since any blood vessel or bleeding does not occur at the position A5, a peak M52 corresponding to the IS/OS can be extracted. In a profile P4 corresponding to A-scan at a position A4, a peak corresponding to the IS/OS is small. Accordingly, the peak cannot be correctly detected. In such a case, it is determined as No in step S602. Such an area is determined as an unidentifiable area in the first-phase processing. Even if determination is made using a fixed threshold value or the like in order to extract the IS/OS, the normal layered structure cannot be extracted due to noise, individual difference, or the like.

Figure 6:
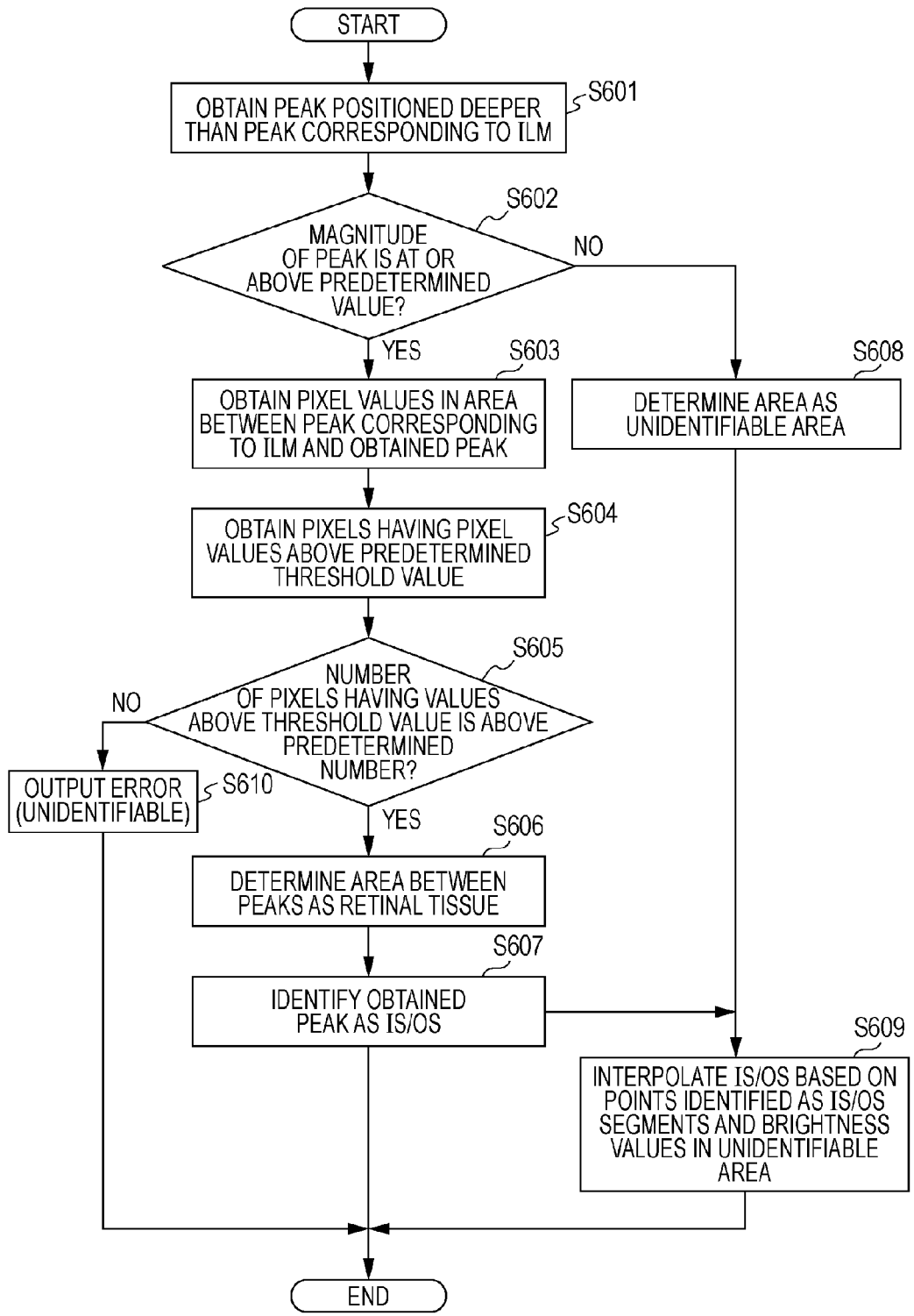
FIG. 6 is a flowchart illustrating the flow of an RPE boundary identifying process by the image processing apparatus.
Figure 7B:
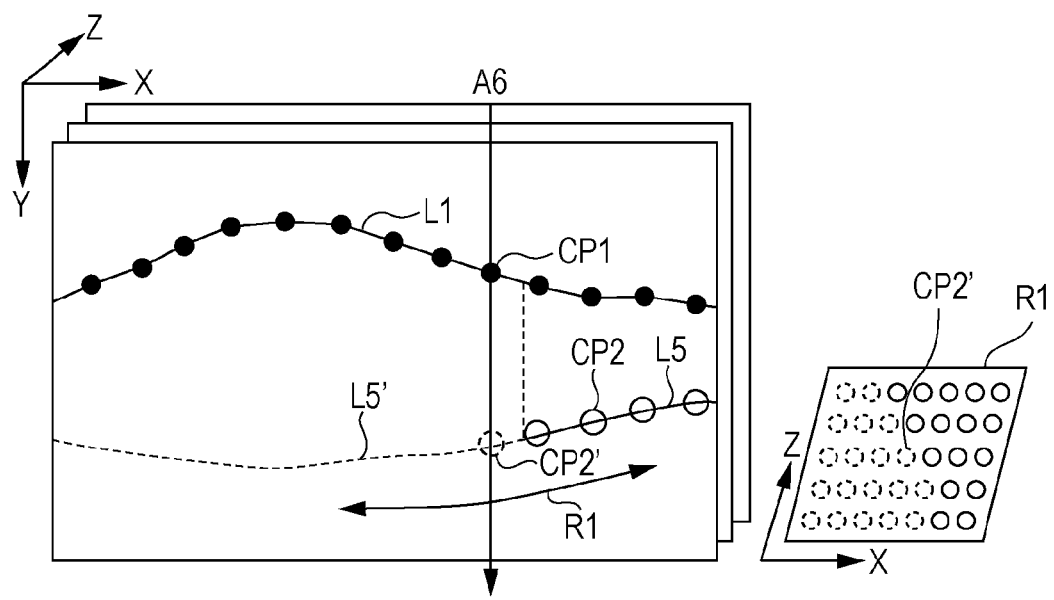

FIG. 7B is a diagram illustrating the details of processing in step S609 in FIG. 6 described above. The boundary of the IS/OS specified in step S607 is indicated by a solid line and part which cannot be identified is indicated by a dashed line.

The remaining IS/OS is to be specified in consideration of the continuity of the magnitudes and positions of the peaks corresponding to the specified IS/OS. In order to take the continuity into consideration on the basis of the magnitudes and positions of the peaks corresponding to the IS/OS specified at the first phase, a local region including a high brightness layered area, located between the IS/OS and the retinal pigment epithelium, at the middle is set in the present embodiment. Peak information is to be extracted from the IS/OS and the retinal pigment epithelium specified in this region. Since the IS/OS is specified for each of the A-scan lines at regular intervals, inner limiting membrane segments CP1 and retinal pigment epithelium segments CP2 which have been specified up to the first phase are arranged at regular intervals, as illustrated in FIG. 7B. Since the IS/OS in an artifact area decreases in brightness, the IS/OS cannot satisfy the specifying conditions at the first phase, so that the IS/OS is not specified. Therefore, a local region is set so as to include an unspecified IS/OS segment at the center. First, a local region R1 on the X-Z plane (C-scan) is set for an A-scan line A6, where the IS/OS is not specified, such that the A-scan line is positioned at the center in the local region R1. The size of the local region is set so as to include 5×7 A-scan lines, serving as the center and surrounding A-scan lines. An average of the magnitudes of the peaks (points indicated by the solid lines in the local region R1), corresponding to the IS/OS segments, specified in the local region and an average of y-coordinate values thereof are calculated. Subsequently, y-coordinate values at which the IS/OS will exist are estimated on the A-scan line at the center of the local region. For the y-coordinate values at which the IS/OS will exist, a set of ten pixels above the calculated average y-coordinate value and ten pixels below it is set to a range and edge components in the Sobel image within the range are examined. The edge component having the closest peak magnitude to the average peak magnitude in the local region is selected from the edge components in the estimated range and the position thereof is specified as the IS/OS. As for the order of identifying the IS/OS at the second phase, identification is started from the A-scan line with the highest rate of specified IS/OS segments in the local region. This processing is repeated in that order, thereby specifying the IS/OS which is difficult to specify due to a reduction in brightness caused by an artifact.

The IS/OS specifying conditions are not limited to the above conditions. For example, the threshold value for the magnitude of the peak corresponding to the IS/OS at the first phase doesn't have to depend on the magnitude of the peak corresponding to the inner limiting membrane. A fixed threshold value may be used. In addition, the size of the local region at the second phase is not limited to the above.

Process for Nerve Fiber Layer Boundary

Figure 8:
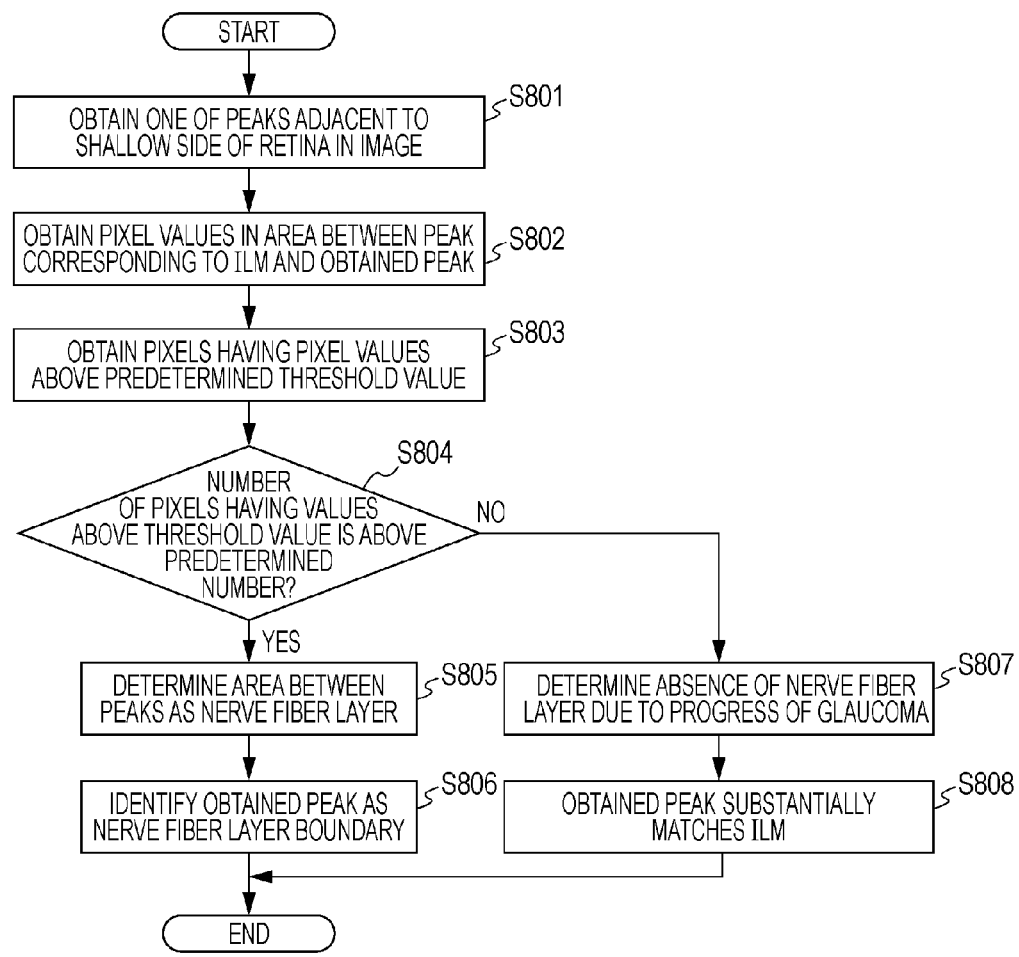
FIG. 8 is a flowchart illustrating the flow of an NFL boundary identifying process by the image processing apparatus.

The details of the processing for identifying the nerve fiber layer boundary L2 in step S308 will be described in accordance with a flowchart of FIG. 8. In step S801, the layered structure identification unit 15 determines a first peak and a second peak and examines brightness values in the area between the peaks in order to specify the nerve fiber layer boundary L2. Specifically, the peak corresponding to the inner limiting membrane L1 identified by the process for identifying the inner limiting membrane is set to the first peak. Referring to FIG. 4, the peak M311 in the profile P31 or the peak M321 in the profile P32 corresponds to the first peak. Subsequently, among the peaks each corresponding to an edge from high to low signal light intensity in the brightness profile P32, the peak which is located below the inner limiting membrane L1 and is the closest thereto is set to the second peak (step S801). In this case, the peak M322 corresponds to the second peak.

In step S802, the layered structure identification unit 15 obtains pixel values in the area between the obtained two peaks by referring to the median image. After that, in step S803, the layered structure identification unit 15 obtains pixels having pixel values above a predetermined threshold value from among the obtained pixels. This processing is performed in order to determine whether the area between the peaks corresponds to the nerve fiber layer L2'.

The nerve fiber layer L2' does not necessarily appear as brightness values (or pixel values) below the inner limiting membrane L1. For example, the nerve fiber layer L2' is not seen on the A-scan line in the vicinity of the macular depression. In order to analyze the nerve fiber layer, therefore, it is first necessary to determine whether the nerve fiber layer L2' exists. According to a method of determining whether the nerve fiber layer L2' exists in the present embodiment, the proportion of pixels each having a value above the product of the average brightness value of the background and 1.5 to the pixels existing between the first peak 321 and the second peak 322 is calculated.

If it is determined in step S804 that the calculated proportion is above ½, the layered structure identification unit 15 determines the area between the peaks as the nerve fiber layer L2' (step S805) and identifies the second peak as the nerve fiber layer boundary L2 (step S806). If the calculated proportion is at or below ½ (No in step S804), it is determined that the nerve fiber layer L2' does not exist between the peaks (step S807). The nerve fiber layer L2' is thin on the target A-scan line and the obtained peak corresponds to the lower boundary of the retinal pigment epithelium L6. In this case, it is medically proven that a lesion, such as progressing glaucoma or a depression, will probably exist.

As described above, whether the tissue between the peaks is the nerve fiber layer L2' is determined on the basis of pixel values (or brightness values) and the nerve fiber layer boundary L2 is specified on the basis of the result of determination. Consequently, the accuracy of identifying a layer boundary can be prevented from being reduced due to glaucoma or a depression.

Second Embodiment

Figure 9:
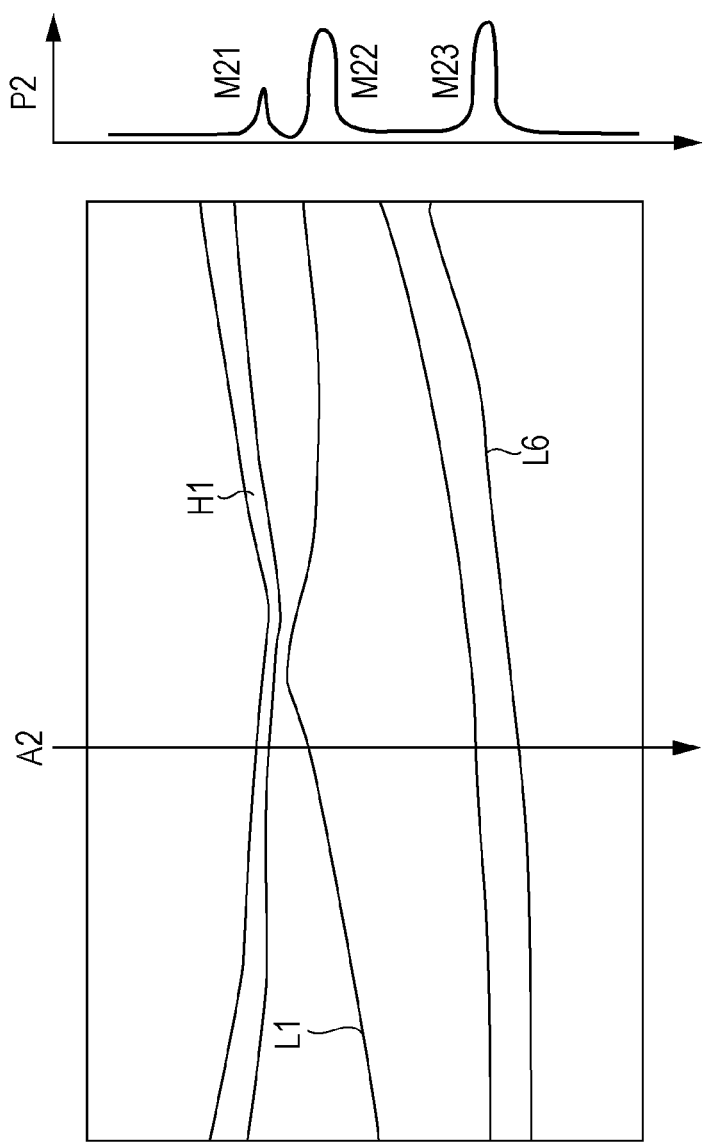
FIG. 9 illustrates an imaging subject and an exemplary brightness profile related to an A-scan line according to a second embodiment.

A second embodiment will be described with respect to a case where the kind of boundary is determined in consideration of the distance between the peaks in step S305 in the first embodiment. In some cases, the detached vitreous cortex H1 is located near the inner limiting membrane L1 as illustrated in the vicinity of an A-scan line A2 in a tomographic image in FIG. 9. It is assumed that the inner limiting membrane L1 is to be specified in the tomographic image. In some cases, since the distance between the peak corresponding to the vitreous cortex H1 and the peak corresponding to the inner limiting membrane L1 is very short on the A-scan line A2, the proportion of high brightness pixels to the background between the peaks is increased due to the thickness of the vitreous cortex H1. According to the present embodiment, a condition for determining a retinal layer boundary is changed depending on the distance between the peaks, so that the retinal layer boundary is identified (determined) with no mistake. As for the flow of a process, the flow is common to the first embodiment, except for the processing for identifying the inner limiting membrane L1. Accordingly, explanation of the common steps to the first embodiment is omitted. Explanation of the common units to the first embodiment is also omitted. The present embodiment differs from the first embodiment in the following point. If the image processing apparatus 10 operates on the basis of an instruction from software, a program stored in the ROM or HDD executes a process of FIG. 10 to realize functions for the process.

Figure 10:
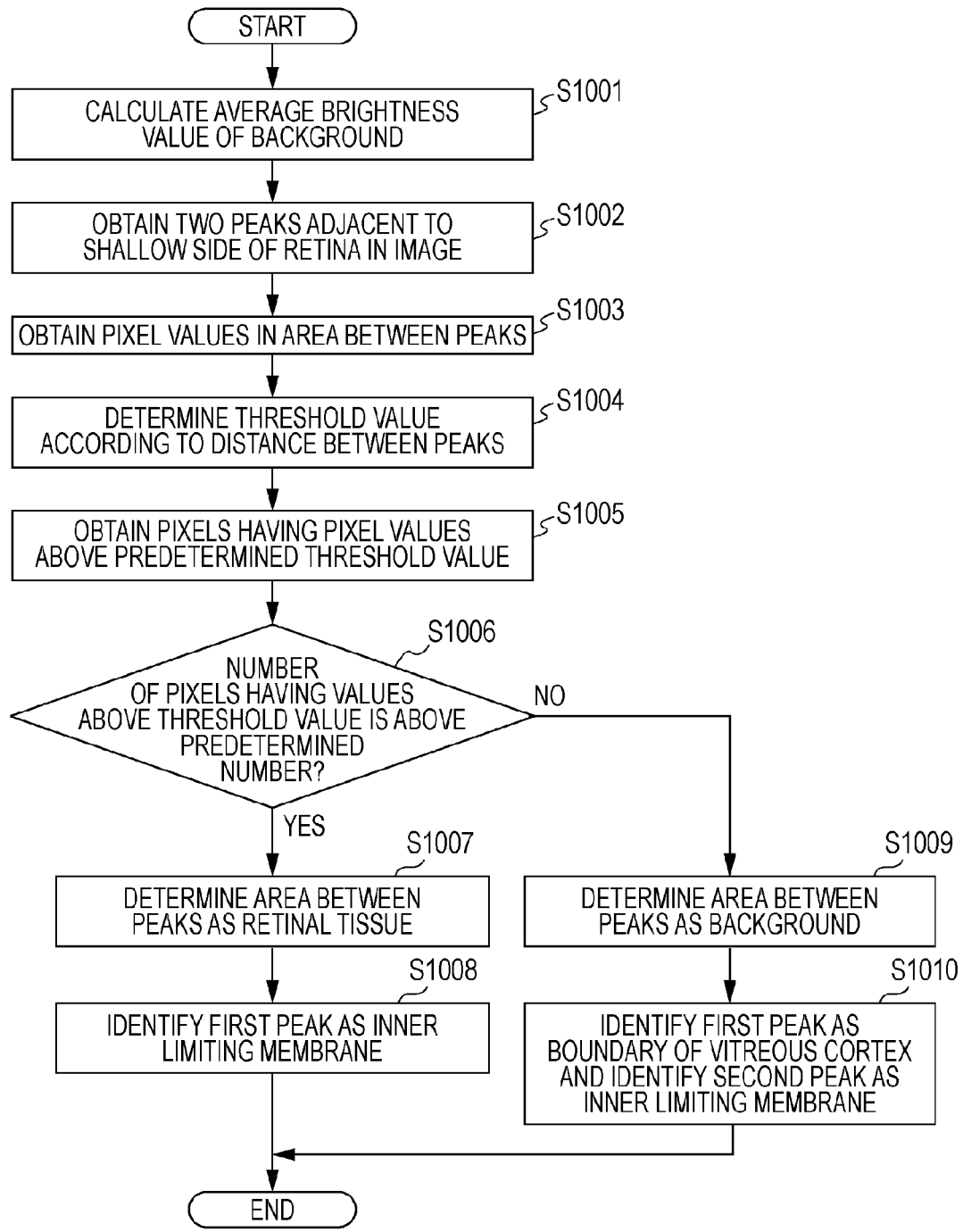
FIG. 10 is a flowchart illustrating the flow of a process by the image processing apparatus according to the second embodiment.

The details of processing for identifying the inner limiting membrane L1 in step S305 according to the second embodiment will be described with reference to FIG. 10. Since processing in steps S1001 to S1003 and steps S1005 to S1010 is the same as that in steps S501 to S509 in the first embodiment, explanation thereof is omitted.

In step S1004, the layered structure identification unit 15 obtains the distance between the peaks in a tomographic image. In this case, the feature point detection unit 14 detects a peak M21 and a peak M22 in the profile P2 on the A-scan line A2 in the order from the shallow side. Assuming that the distance between the peaks is shorter than ten pixels, when the proportion of pixels each having a pixel value above the product of the average grayscale value of the background and 1.2 to the pixels in the area between the peaks is above ¾, it is determined that the retinal tissue exists between the peaks. Thus, the first peak is determined as the inner limiting membrane L1. When the proportion is at or below ¾, it is determined that the area between the peaks corresponds to the background. The second peak is determined as the inner limiting membrane L1. In the case where the distance between the peaks is equal to or longer than ten pixels, a threshold value indicating the proportion is set to ½ in the same way as step S205 in the first embodiment. The reason why the threshold value is changed depending on the distance between the peaks is that a boundary at the position corresponding to each peak constitutes a layer having a predetermined thickness and its influence is large. For example, the vitreous cortex H1 detached from the retinal layer has a predetermined thickness. When the boundary between the vitreous cortex H1 and the background is detected as the first peak M21, the boundary between the gap (background) caused by the detachment and the inner limiting membrane L1 is detected as the second peak M22, the thickness of the vitreous cortex H1 affects determination, thus resulting in determination error. In addition, if two boundaries are in tight contact with each other, the amount of information about the area between the boundaries is relatively small. In some cases, the information about the area between the boundaries cannot be correctly obtained due to the boundaries. It is therefore necessary to change a threshold value depending on the distance between the peaks. Particularly, when the distance between the boundaries is reduced, the threshold value indicating the proportion has to be increased. In addition to changing the threshold value indicating the proportion, a threshold pixel value may be changed.

According to this process, the condition for specifying the inner limiting membrane L1 is changed depending on the distance between the peaks. Advantageously, even if the boundaries are in tight contact with each other, error in identifying the inner limiting membrane can be reduced.

Other Embodiments

In the first embodiment, the image transformation unit 12 transforms an input image. Brightness values of an original image may be used as inputs for the next step without image transformation and brightness information generated by the brightness information generation unit 13 may be directly generated from the original image.

In the first and second embodiments, tissue existing between the peaks is determined. Determination is not limited to this. For example, pixel values of areas on opposite sides of each peak in a predetermined range may be compared with pixel values of the background (vitreous body) on each A-scan line to determine tissue on the opposite sides of the peak, thereby identifying the kind of layer boundary corresponding to the peak. According to this process, even if a plurality of peaks corresponding to layer boundaries are not found, the position of a peak can be specified in the retinal layers. This makes it difficult to cause error in identifying the kind of layer boundary. In addition, detection and determination may be performed not for each A-scan line but in a predetermined two-dimensional area.

In the first and second embodiments, comparison with a pixel value of the vitreous body is performed. The application of the present invention is not limited to such comparison. A predetermined reference value may be used as a substitute. For example, when an image is represented using 256 grayscale values, a grayscale value of 0 may be used as a reference value.

A program that realizes the functions in the above-described embodiments may be supplied to a computer or a system through a network or a storage medium. In this case, it is needless to say that an aspect of the present invention includes an apparatus or system that stores, reads out, and executes the supplied program, the program, or the storage medium itself.

Furthermore, the above-described embodiments have been described with respect to the case where the present invention is realized by software. The application of the present invention is not limited to this. For example, it is easily possible for those skilled in the art that the present invention belongs to mount the above-described functional blocks on a circuit, or realize them by hardware. In addition, part of the functional blocks executed through the program in the embodiments may be mounted onto a dedicated image processing board.

According to the present invention, the kind of boundary can be identified on the basis of not only information about the boundary but also characteristics of the vitreous body corresponding to the background of a tomographic image of the retina and those between boundaries. Advantageously, identification error can be reduced.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of International Application No. PCT/JP2009/070924, filed Dec. 15, 2009, which is hereby incorporated by reference herein in its entirety.

REFERENCE SIGNS LIST

10 image processing apparatus
11 image acquisition unit
12 image transformation unit
13 brightness information generation unit
14 feature point detection unit
15 layered structure identification unit
16 image display unit
20 tomographic image acquisition device
30 storage unit

The invention claimed is:
1. An image processing apparatus comprising:
a memory; and
a processor that is in communication with the memory, the processor configured to control a detection unit configured to detect a first layer boundary and a second layer boundary in a tomographic image of a subject's eye;
a determination unit configured to determine whether an area between the first layer boundary and the second layer boundary is a gap caused by a detachment of vitreous cortex or not; and
an identifying unit configured to identify the kind of the first layer boundary on the basis of the result of the determination,
wherein the first layer boundary is identified as an inner limiting membrane when it is determined that the area is not the gap caused by the detachment of vitreous cortex and the first layer boundary is identified as a vitreous cortex when it is determined that the area is the gap caused by the detachment of vitreous cortex.

2. The image processing apparatus according to claim 1, wherein the determination unit compares the characteristics of the area between the first layer boundary and the second layer boundary with those of an area of a vitreous body in the tomographic image to determine whether the area between the first layer boundary and the second layer boundary is the gap caused by the detachment of vitreous cortex or not, and
wherein the identifying unit identifies the kind of the first layer boundary on the basis of the result of determination.

3. The image processing apparatus according to claim 1, wherein the determination unit changes a threshold value for the determination depending on the distance between the first layer boundary and the second layer boundary.

4. The image processing apparatus according to claim 1, wherein the identification unit identifies the kind of the first boundary layer in accordance with the magnitude of the difference between a pixel value based on an area corresponding the vitreous body and that of the area between the first layer boundary and the second layer boundary and the proportion of pixels each having the difference at or above a predetermined value to pixels in the area between the first layer boundary and the second layer boundary.

5. The image processing apparatus according to claim 1, wherein the detecting unit detects, as the boundary of a layer in the retina, a point at which a change in pixel value or brightness value in the depth direction of the tomographic image is at or above a predetermined value.

6. The image processing apparatus according to claim 1, wherein
the detecting unit detects at least part of the boundary of each layer on the basis of an edge corresponding to the layer in the depth direction of the tomographic image and detects the boundary of the layer in an area where the boundary is not detected on the basis of the detected part of the boundary and pixel values in the area where the boundary is not detected.

7. The image processing apparatus according to claim 1, wherein the tomographic image of the subject's eye is a tomographic image of the retina of the subject's eye.

8. The image processing apparatus according to claim 1, wherein the tomographic image of the subject's eye is an image captured by an optical coherence tomography (OCT) image pickup device.

9. The image processing apparatus of claim 1, further comprising:
an acquisition unit configured to acquire a tomographic image of a subject's eye generated on the basis of signal light applied to the retina of the subject's eye, wherein; the identification unit comprises a first identification unit and a second identification unit,
the first identification unit is configured to identify the inner limiting membrane or the retinal pigment epithelium on the basis of an edge from low to high intensity of the signal light obtained from the acquired tomographic image, and
the second identification unit is configured to identify, on the basis of an edge from high to low intensity of the signal light obtained from the tomographic image of the subject's eye, a layer or the boundary of the layer existing in an area between the inner limiting membrane or the retinal pigment epithelium and the edge.

10. The image processing apparatus of claim 1, further comprising:
a display unit configured to display the result of identification with the tomographic image.

11. The image processing apparatus of claim 1, wherein the detection unit detects the first layer boundary and the second layer boundary based on a change point of a pixel or brightness value in the tomographic image, and
wherein the determination unit determines whether the area between the first layer boundary and the second layer boundary is the gap or not based on an average brightness value of an area of a vitreous body in the tomographic image.

12. A method for image processing, comprising:
detecting a first layer boundary and a second layer boundary in a tomographic image of a subject's eye;
determining whether an area between the first layer boundary and the second layer boundary is a gap caused by a detachment of vitreous cortex or not; and
identifying the kind of the first layer boundary on the basis of the result of the determination,
wherein the first layer boundary is identified as an inner limiting membrane when it is determined that the area is not the gap caused by the detachment of vitreous cortex and the first layer boundary is identified as a vitreous cortex when it is determined that the area is the gap caused by the detachment of vitreous cortex.

13. A non-transitory computer-readable storage medium containing a program that allows a computer to execute:
a process of detecting a first layer boundary and a second layer boundary in a tomographic image of a subject's eye;
a process of determining whether an area between the first layer boundary and the second layer boundary is a gap caused by a detachment of vitreous cortex or not; and
a process of identifying the kind kinds of the first layer boundary and the second layer boundary on the basis of the result of the determination,
wherein the first layer boundary is identified as an inner limiting membrane when it is determined that the area is not the gap caused by a detachment of vitreous cortex and the first layer boundary is identified as a vitreous cortex when it is determined that the area is the gap caused by a detachment of vitreous cortex.

* * * * *